United States Patent
Christopherson et al.

(10) Patent No.: US 7,087,017 B2
(45) Date of Patent: Aug. 8, 2006

(54) ATRAUMATIC SENSOR LEAD ASSEMBLIES

(75) Inventors: Mark A. Christopherson, Shoreview, MN (US); Nancy Perry Pool, Minnetonka, MN (US); John L. Sommer, Coon Rapids, MN (US); Eric Bonde, Victoria, MN (US)

(73) Assignee: Medtronic, Inc., Minneapolis, MN (US)

( * ) Notice: Subject to any disclaimer, the term of this patent is extended or adjusted under 35 U.S.C. 154(b) by 162 days.

(21) Appl. No.: 10/284,897

(22) Filed: Oct. 31, 2002

(65) Prior Publication Data

US 2004/0087847 A1   May 6, 2004

(51) Int. Cl.
*A61B 5/00* (2006.01)
(52) U.S. Cl. ..................... 600/300; 600/365
(58) Field of Classification Search ............... 600/300, 600/301, 486, 585; 607/9, 36, 122–129, 607/119, 37; 606/108, 129
See application file for complete search history.

(56) References Cited

U.S. PATENT DOCUMENTS

| | | | | |
|---|---|---|---|---|
| 4,403,984 A | * | 9/1983 | Ash et al. | 604/503 |
| 4,644,960 A | * | 2/1987 | Johans | 607/122 |
| 4,899,760 A | | 2/1990 | Jaeb et al. | |
| 4,936,826 A | | 6/1990 | Amarasinghe | |
| 4,954,129 A | * | 9/1990 | Giuliani et al. | 604/540 |
| 5,174,303 A | | 12/1992 | Schroeppel | 128/786 |
| 5,261,892 A | * | 11/1993 | Bertaud et al. | 604/171 |
| 5,484,404 A | | 1/1996 | Schulman et al. | |
| 5,593,430 A | | 1/1997 | Renger | |
| 5,605,152 A | | 2/1997 | Slate et al. | |
| 5,651,767 A | | 7/1997 | Schulman et al. | |
| 5,797,898 A | | 8/1998 | Santini, Jr. et al. | |
| 5,824,030 A | | 10/1998 | Yang et al. | |
| 5,843,141 A | | 12/1998 | Bischoff et al. | |
| 5,897,585 A | | 4/1999 | Williams | |
| 5,919,160 A | | 7/1999 | Sanfilippo, II | |
| 5,954,643 A | * | 9/1999 | VanAntwerp et al. | 600/316 |
| 5,985,129 A | | 11/1999 | Gough et al. | |
| 5,999,848 A | | 12/1999 | Gord et al. | |
| 6,192,280 B1 | | 2/2001 | Sommer et al. | |
| 6,258,058 B1 | | 7/2001 | Sanfilippo, II | |
| 6,328,699 B1 | * | 12/2001 | Eigler et al. | 600/486 |
| 2001/0049502 A1 | | 12/2001 | Chen | |
| 2002/0120186 A1 | | 8/2002 | Keimel | |

* cited by examiner

*Primary Examiner*—Max F. Hindenburg
*Assistant Examiner*—Patricia C. Mallari
(74) *Attorney, Agent, or Firm*—Michael C. Soldner; Girma Wolde-Michael

(57) ABSTRACT

The invention is directed to lead configurations for sensors that allow for less invasive sensor replacement procedures. In one configuration, a sensor lead assembly includes an outer lead body and an inner lead including a sensor such as an electrochemical glucose sensor. The inner lead can be positioned in an inner conduit of the outer lead body. The outer lead body may be substantially permanently implanted in the patient, and the inner lead can be implanted through the inner conduit of the outer lead body. Once the sensor of the inner lead has worn out or otherwise exhausted its useful life, the inner lead can be removed, and a new inner lead can be implanted in place of the old inner lead.

1 Claim, 8 Drawing Sheets

ATRAUMATIC SENSOR LEAD ASSEMBLIES

TECHNICAL FIELD

The invention relates to implantable medical devices (IMDs) and, more particularly, implantable leads that include implantable sensors for sensing conditions within a patient.

BACKGROUND

Sensors facilitate the sensing of certain conditions within a patient. An implantable medical device (IMD) may include circuitry electrically coupled to one or more sensors to record patient conditions over time. For example, an implantable lead is typically used to couple a sensor to circuitry within an IMD housing.

As one example, electrochemical sensors are commonly used for diabetes patients, e.g., to monitor a patient's glucose levels. In that case, a lead can be implanted within a patient to deploy an electrochemical glucose sensor for sensing levels of glucose in the patient's blood stream. A distal end of the lead, which includes the electrochemical glucose sensor, may be positioned in the patient's blood stream, e.g., within a heart chamber. A proximal end of the lead may be coupled to circuitry within the IMD. The IMD may record the sensed conditions, which may be sent to an external programmer via telemetry, so that a physician can monitor the patient's blood glucose levels. Alternatively or additionally, the IMD may interpret the sensed conditions and possibly deliver therapy to the patient, e.g., by delivering doses of insulin or drug therapy to the patient if sensed glucose levels exceed one or more therapy thresholds.

Most glucose sensors use electrochemical methods such as an electroenzymatic method in which blood glucose is oxidized under glucose-oxidase control, producing gluconic acid and hydrogen peroxide. In that case, the electrochemical glucose sensor can be used to sense levels of gluconic acid and/or hydrogen peroxide in order to estimate a patient's glucose levels. Alternatively, the glucose levels may be determined or sensed more directly by the electrochemical glucose sensor. In any case, an electrochemical glucose sensor on a medical lead facilitates a chemical process which can be identified by electrical signals to measure a patient's glucose levels.

In addition to electrochemical glucose sensors a number of other types of electrochemical sensors have been developed to measure blood chemistry or the chemistry of other bodily fluids or material. In general, electrochemical sensors make use of one or more chemical processes and electrical signals can be used to measure conditions sensed by the chemical processes. Other types of sensors also exist including pressure sensors, optical sensors, and various other types of sensors.

Electrochemical sensors and many other types of sensors, however, typically suffer from stability and longevity problems. For example, the electrochemical process used by electrochemical glucose sensors can cause significant depletion of the glucose sensors over time, eventually causing the glucose sensor to be ineffective for monitoring levels of glucose in the patient's blood stream. Similarly, other sensors often have similar problems in that prolonged use causes depletion, wear or tissue overgrowth, which can undermine the sensing capabilities of the given sensor.

Sensor replacement is a major concern because replacement of conventional electrochemical sensor leads is typically a very invasive medical procedure in which a lead is removed from a patient's blood vessel, and a new lead is inserted to a high blood flow location, such as inside a heart chamber. In the replacement procedure, the new electrochemical sensor lead is typically inserted through the same blood vessel used for the previous electrochemical sensor lead. Removal of the lead can be very traumatic because of fibrosis around the lead. Moreover, repeated implantation of new leads can cause damage and scarring to the patient's blood vessel, making subsequent implantation more difficult and more dangerous to the patient. Infection is also a concern.

SUMMARY

In general, the invention is directed to atraumatic lead configurations for sensors that allow for less invasive sensor replacement procedures. In one configuration, a sensor lead assembly includes an outer lead body and an inner lead including a sensor. The sensor may comprise an electrochemical sensor, or another sensor for which replacement during the life of the patient is anticipated. The inner lead can be positioned within an inner conduit defined by the outer lead body. The outer lead body may be permanently implanted in the patient and removably attached to an implantable medical device. The inner lead can be implanted through the inner conduit of the outer lead body. Moreover, once the electrochemical sensor of the inner lead has been depleted or otherwise exhausted its useful life, the inner lead can be removed, and a new inner lead can be implanted in place of the old inner lead. Importantly, this replacement procedure is much less invasive and less traumatic than conventional lead replacement procedures. For example, while the outer lead body remains substantially in place, the replaceable inner lead avoids substantial contact and attachment to blood vessel tissue during replacement and use.

In an alternative configuration, the outer lead body may define a window that exposes one of a plurality of electrochemical sensors positioned along axial positions of the inner lead. In that case, when a first sensor has been depleted, become overgrown with tissue, or otherwise exhausted its useful life, the inner lead may be axially repositioned relative to the window of the outer lead body to expose a new electrochemical sensor. In some cases, this repositioning of the inner lead relative to the window of the outer lead body may be performed by an implantable medical device (IMD), avoiding a re-implantation procedure altogether.

In one embodiment, the invention provides an electrochemical lead assembly comprising an outer lead body for substantially permanent implantation in a patient. The outer lead body can be formed with an inner conduit. The electrochemical lead assembly may also include an inner lead positioned in the inner conduit of the outer lead body, the inner lead including an electrochemical sensor positioned in proximity to a distal end of the inner lead.

In another embodiment, the invention provides an implantable medical device, such as an implantable sensing device for sensing patient conditions. For example, the implantable medical device may include a housing including circuitry for storing sensed conditions, and an outer lead body mechanically coupled to the housing. The outer lead body can be formed with a conduit. The implantable medical device may also include an inner lead positioned in the conduit of the outer lead body and electrically coupled to the circuitry in the housing at a first end of the inner lead. The inner lead may include an electrochemical sensor positioned in proximity to a distal end of the inner lead, or another type of sensor for which replacement is commonly anticipated.

In another embodiment, the invention provides an outer lead body for substantially permanent implantation in a patent. The outer lead body may include a first end formed for mechanical attachment to an implantable medical device, and a second end formed with a seal to be pierced by an inner lead. A conduit for receiving the inner lead may be formed in the outer lead body between the first and second end.

In another embodiment, the invention provides an inner lead. The inner lead may include a lead body defining a first end and a second end, and a plurality of sensors formed along axial positions of the lead body in proximity to the first end. The lead may also include an electrical contact formed on the lead body in proximity to the first end, wherein each of the sensors is electrically coupled to the electrical contact.

In another embodiment, the invention provides a method comprising removing a first lead including a first sensor from an implanted outer lead body, and inserting a second lead including a second sensor into the implanted outer lead body.

In another embodiment, the invention provides a method comprising positioning an inner lead relative to a window of an outer lead body to expose a first sensor, and repositioning the inner lead relate to the window of the outer lead body to expose a second sensor.

The invention may be capable of providing a number of advantages. In particular, the invention can greatly simplify, or in some cases, eliminate implantation procedures for electrochemical sensor replacement. As mentioned above, electrochemical sensor replacement, and other types of sensor replacement is a major concern because replacement of conventional sensor leads is typically a very invasive medical procedure in which a lead is removed from a patient's blood vessel, and a new lead is inserted. The invention provides various alternatives to conventional lead replacement that are much less invasive and traumatic to a patient. In this manner, the invention can improve patient care and comfort, avoid infection, and generally improve therapy to the patient. Moreover, to the extent conventional sensor replacement is a barrier to patient care, the invention may remove the barrier, possibly causing physicians to be more willing to use sensors in patient care.

Additional details of various embodiments are set forth in the accompanying drawings and the description below. Other features, objects and advantages will become apparent from the description and drawings, and from the claims.

DETAILED DESCRIPTION

The invention is directed to lead configurations for sensors that allow for atraumatic sensor replacement procedures. Various embodiments of the invention are directed to implantable medical devices (IMDs), lead assemblies, outer lead bodies, inner leads, and various sensor replacement methods, including improved implantation procedures that may be executed by a physician, as well as sensor replacement procedures that may be executed by an IMD.

In one configuration, a sensor lead assembly includes an outer lead body and an inner lead including an electrochemical sensor. The inner lead may be positioned within an inner conduit defined by the outer lead body. The lead assembly may be connected to a housing of an IMD. The outer lead body may be substantially permanently implanted in the patient, and the inner lead can be implanted through the conduit of the outer lead body. Then, once the electrochemical sensor of the inner lead has been depleted, become overgrown with tissue, or otherwise exhausted its useful life, the inner lead can be removed, and a new inner lead can be implanted to replace the old inner lead with the depleted sensor. The replacement procedure associated with this embodiment may be executed by a physician, but may be much less invasive and traumatic than conventional lead replacement procedures. For example, the replacement procedure may be subcutaneous.

In an alternative configuration, the outer lead body may define a window that exposes one of a plurality of electrochemical sensors positioned along axial positions of the inner lead. A physician may reposition the inner lead relative to the window to expose a new electrochemical sensor, or alternatively, an IMD may be programmed to reposition the inner lead relative to the window to expose a new electrochemical sensor, e.g., upon determining that the previously exposed electrochemical sensor has worn out. Accordingly, the replacement procedure associated with this embodiment may be executed by a physician or an IMD. In particular, the IMD may include a motor or other actuator capable of causing axial displacement of the inner lead. If executed by the IMD, the replacement procedure may avoid a subsequent implantation procedure altogether.

Many details provided below with respect to electrochemical sensors may find useful application with a wide variety of other types of sensors including oxygen sensors, pressure sensors, optical sensors, and many other types of sensors. In many cases, the sensors are non-electrode sensors, i.e., non-stimulative. If removal or replacement of the non-electrode sensor is desirable, then the teaching herein may be used to replace the sensor lead in response to such tissue overgrowth.

Figure 1:
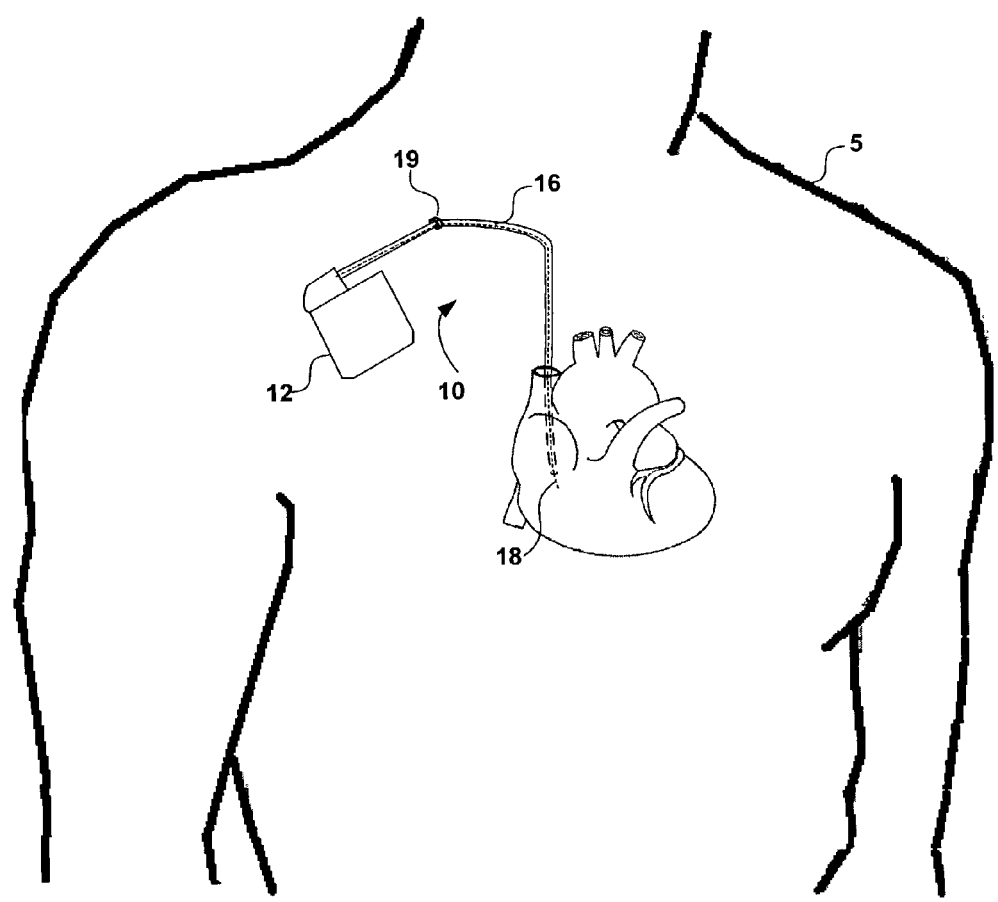
FIG. 1 is a conceptual diagram illustrating an exemplary implantable medical device (IMD) in a human body.

FIG. 1 is a conceptual diagram illustrating an exemplary implantable medical device (IMD) 10 in a human body 5. A similar device may also be used with other living beings. IMD 10 comprises a housing 12 containing various circuitry that controls IMD operations and records sensed events. Housing 12 is typically hermetically sealed to protect the circuitry. Housing 12 may also house an electrochemical cell, e.g., a lithium battery for powering the circuitry, or other elements. The circuitry within housing 12 may be coupled to an antenna to transmit and receive information via wireless telemetry signals. Accordingly, conditions sensed by IMD 10 may be sent to an external programmer so that a physician can examine the sensed conditions for diagnostic purposes.

IMD 10 also comprises a lead assembly that includes an outer lead body 16 and an inner lead 18 positioned within an inner conduit of outer lead body 16. Outer lead body 16 may be implanted through a blood vessel of human body 5 and fed into a heart chamber. An anchoring structure 19 may anchor outer lead body 16 in proximity to its entry point into the venous system. As outlined in greater detail below, outer lead body 16 can be implanted in human body 5 in a substantially permanent manner. In other words, outer lead body 16 may remain implanted within body 5 even though inner lead 18 may be withdrawn and replaced from time to time. Accordingly, inner lead 18 comprises a removable lead that can be removed from the conduit of outer lead body 16 without removing outer lead body 16 from human body 5. In particular, inner lead 18 can be removed from human body 5 and replaced with a relatively simple replacement procedure that is much less invasive and much less traumatic than conventional implantation procedures.

Inner lead 18 comprises a lead body that includes an electrochemical sensor in proximity to a distal tip of inner lead 18, or another sensor element that has a relatively short useful life. Electrochemical sensors refer to sensors that make use of one or more chemical processes and electrical signals. In particular, the electrical signals may change with certain chemical processes and thereby identify conditions in a patient. Several types of electrochemical sensors have been developed including electrochemical glucose sensors, electrochemical oxygen sensors, and the like. The problem with such electrochemical sensors, however, is that they generally have a relatively short useful life. In particular, the chemical processes can cause corrosion and depletion of the electrochemical sensor, which eventually renders the sensor ineffective for its sensing purposes. Tissue overgrowth may also render the sensor ineffective. When the sensor is rendered ineffective, the electrochemical sensor typically requires replacement. The "outer-inner" lead assembly configuration described herein is one example of a lead assembly that can facilitate less invasive and less traumatic sensor replacement than conventional implantation. The invention may find useful application with electrochemical sensor leads, or other types of sensor leads having relatively short useful lives.

IMD 10 may comprise sensing device that senses conditions of human body 5 and stores the sensed conditions. As mentioned, IMD 10 may support telemetry communication with an external programmer in order to allow the sensed information to be delivered to a physician for analysis. The invention, however, is not necessarily limited to use with passive sensing devices, but may also find application in devices that actively deliver therapy to the patient. In that case, the circuitry in housing 12 may interpret sensed conditions, and deliver therapy to human body 5 in response to the sensed conditions. For example, the therapy may comprise therapeutic electrical pulses, drug delivery, or the like.

In the description that follows, many details of the invention will be described with reference to an IMD that performs glucose sensing functions for diabetes patients. In that case, the electrochemical sensor on the distal tip of inner lead 18 would comprise a electrochemical glucose sensor positioned in a high blood flow location such as in a chamber of the heart. Again, however, the invention is not necessarily limited to glucose sensors, or even electrochemical sensors, and may find useful application in any sensor applications in which sensor replacement is commonly required. In some cases, the sensors may be non-electrode sensors for which tissue overgrowth over the sensor is generally undesirable.

Diabetes mellitus is the most common of endocrine disorders, and is characterized by inadequate insulin action. Diabetes mellitus has two principal variants, known as Type I diabetes and Type II diabetes. The latter is also referred to as DM/II (diabetes mellitus type II), adult-onset diabetes, maturity-onset diabetes, or NIDDM (non-insulin dependent diabetes mellitus).

Type I diabetes is usually diagnosed in children and young adults. In Type I diabetes, the body does not produce insulin. Insulin is necessary for the body to be able to use sugar. When sugar builds up in the blood instead of going into cells, it can cause problems such as a short-term lack of energy, and longer term problems with eyes, kidneys, nerves, the heart, or other organs or systems.

Type II diabetes generally develops in adulthood, and the risk of development of Type II diabetes generally increases with age. Factors such as obesity also contribute to the risk. A patient suffering from Type II diabetes secretes insulin, but the insulin's target cells are less sensitive to insulin. Symptoms of Type II diabetes are typically slow to appear, and a patient having Type II diabetes may not be aware of his condition. A blood test may show whether the patient has impaired glucose tolerance (IGT), which is often a precursor to Type II diabetes, or compensated Type II diabetes. Unless addressed with treatment such as diet and exercise, these conditions may develop into uncompensated Type II diabetes, a very serious condition.

Patients that have diabetes as well as at patients at risk for diabetes may use an IMD that includes a glucose sensor, e.g. to monitor levels of blood sugar. Most glucose sensors use electrochemical methods such as an electroenzymatic method in which blood glucose is oxidized under glucose-oxidase control, producing gluconic acid and hydrogen peroxide. In that case, the electrochemical glucose sensor can be used to sense levels of gluconic acid and/or hydrogen peroxide in order to estimate a patient's glucose levels. Alternatively, the glucose levels may be determined or sensed more directly by the electrochemical glucose sensor. In any case, an electrochemical glucose sensor on a lead facilitates a chemical process. Electrical signals can be used to identify these chemical processes on the electrochemical sensor in order to identify certain conditions indicative of a patient's glucose levels. Optical glucose sensors are also used in some cases, and may likewise benefit from the teaching herein.

Figure 2:
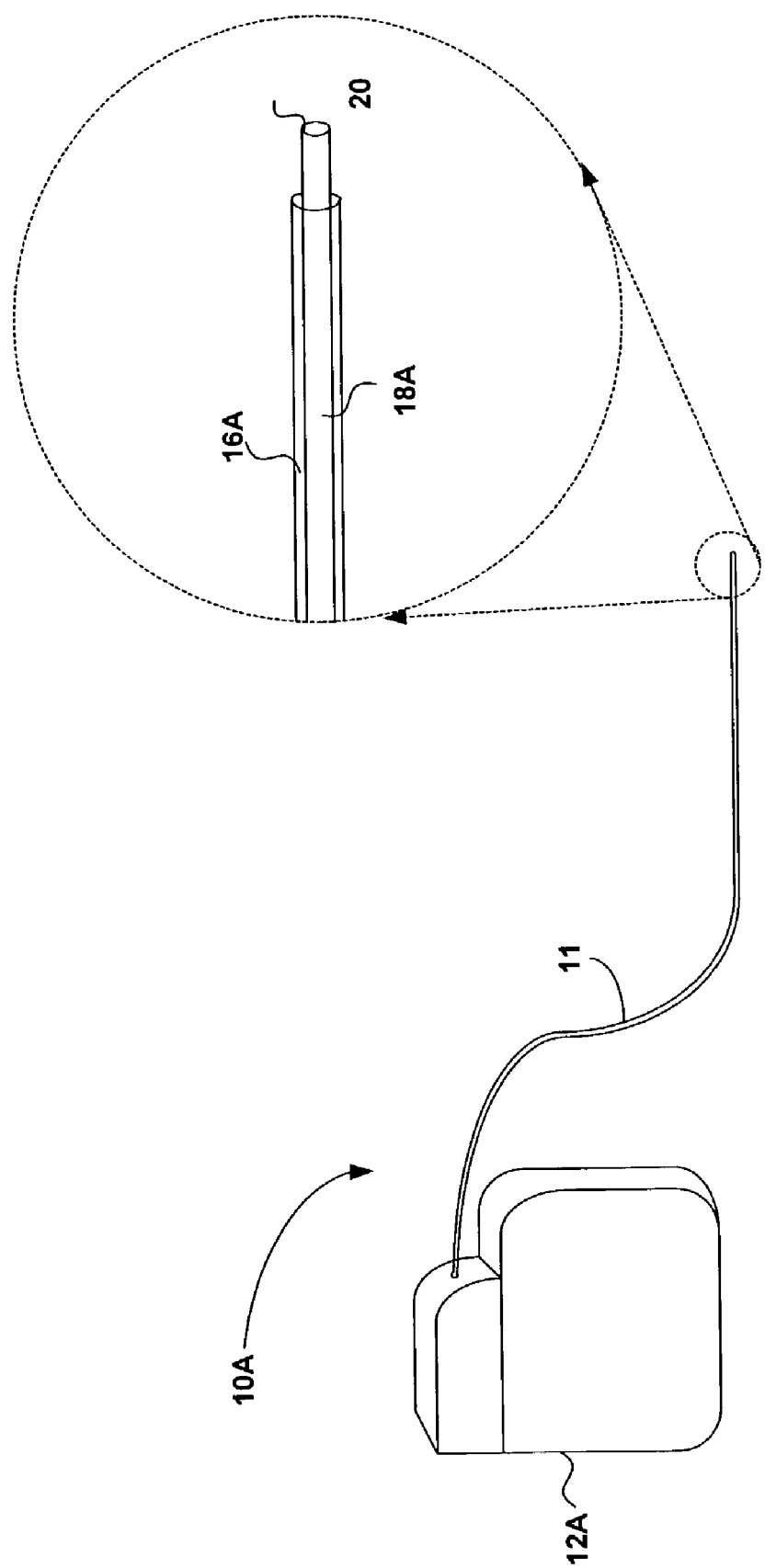
FIG. 2 is a simplified schematic view of an exemplary IMD with an enlarged view of a distal end of an exemplary implantable lead assembly.

FIG. 2 is a simplified schematic view of an exemplary glucose sensing IMD 10A with an enlarged view of a distal end of an exemplary implantable lead assembly. IMD 10A comprises a housing 12A which houses various circuitry that controls glucose sensing operations and records sensed events. IMD 10A also comprises a lead assembly 11 that includes an outer lead body 16A and an inner lead 18A positioned within a conduit of outer lead body 16A.

Outer lead body 16A may be implanted through a blood vessel such as the superior vena cava of a patient to feed the distal end 20 of inner lead 18A into a high blood flow location. For example, distal end 20 of inner lead 18A may be placed in a heart chamber such as the right atrium. The distal end 20 of inner lead 18A includes a glucose sensor for sensing glucose in the patients blood, e.g., an electrochemical glucose sensor. Again, outer lead body 16A is generally implanted in the patient in a substantially permanent manner. Inner lead 18A, on the other hand, comprises a removable lead that can be removed from the conduit of outer lead body 16A without removing outer lead body 16A from the patient. Accordingly, inner lead 18A can be removed from the conduit of outer lead body 16A and replaced with a relatively simple replacement procedure that is much less invasive and much less traumatic than conventional implantation procedures.

Figure 3:
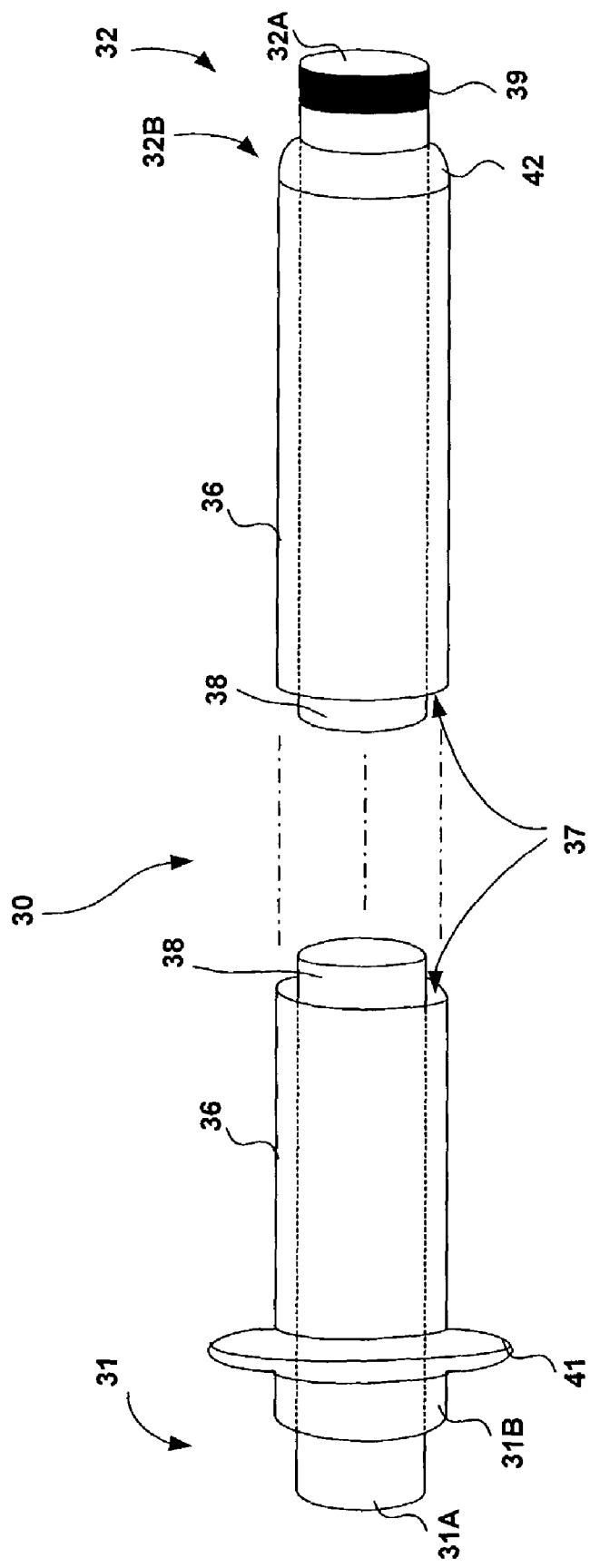
FIG. 3 is a simplified schematic of first and second ends of an exemplary implantable lead assembly including an outer lead body and an inner electrochemical lead.

FIG. 3 is a simplified schematic view of first and second ends 31, 32 of an exemplary implantable lead assembly 30 including an outer lead body 36 and an inner lead 38 that includes an electrochemical sensor 39 such as an electrochemical glucose sensor. As illustrated in FIG. 3, outer lead body 36 defines a conduit 37 sized to receive inner lead 38. Likewise, inner lead 38 is sized for insertion into the conduit 37 of outer lead body 36. Inner lead 38 has sufficient rigidity to allow insertion and removal from conduit 37, and may include a lubrication layer to improve insertion or removal. A stylet or other structural enhancement may be used to provide added rigidity to inner lead 38 during insertion or removal.

A first end 31A of inner lead 38 can be electrically coupled to an IMD. A second end 32A (the distal end) of inner lead 38 includes electrochemical sensor 39. Electrical signals can be used to measure chemical reactions that occur on sensor 39 in order to measure glucose levels in a patient. Again, however, electrochemical sensor 39 is only one example of a sensor that may be used on an inner lead in accordance with the invention. Pressure sensors, optical sensors, biological sensors, and a wide variety of non-electrode sensors for which tissue overgrowth is undesirable may benefit from the teaching herein.

The first and second ends 31B and 32B of outer lead body 38 are formed with sealing mechanisms. In particular, first end 31B of outer lead body 36 is formed for sealed attachment to an IMD. For example, protruding features 41 may be formed on outer lead body 36 in proximity to first end 31 to facilitate attachment to an IMD in a sealed fashion to ensure that body fluid cannot enter conduit 37. The second end 32B of outer lead body 36 may be formed with a seal 42 that is pierced by inner lead 38 upon insertion of inner lead through conduit 37. By way of example, seal 42 may comprise a silicone material to ensure that fluid cannot penetrate into conduit 37.

Figure 4:
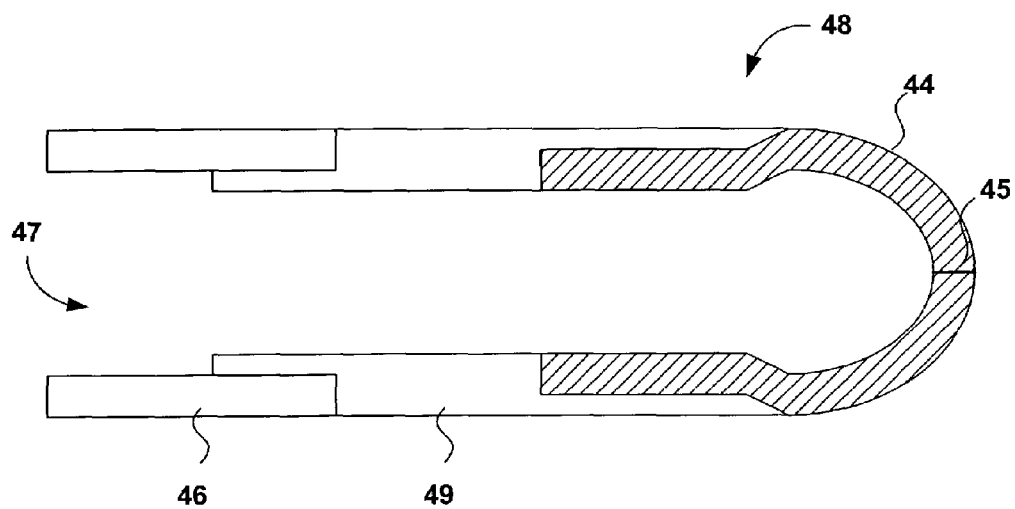
FIGS. 4 and 5 are enlarged cross-sectional views of distal ends of exemplary outer lead bodies.
Figure 5:
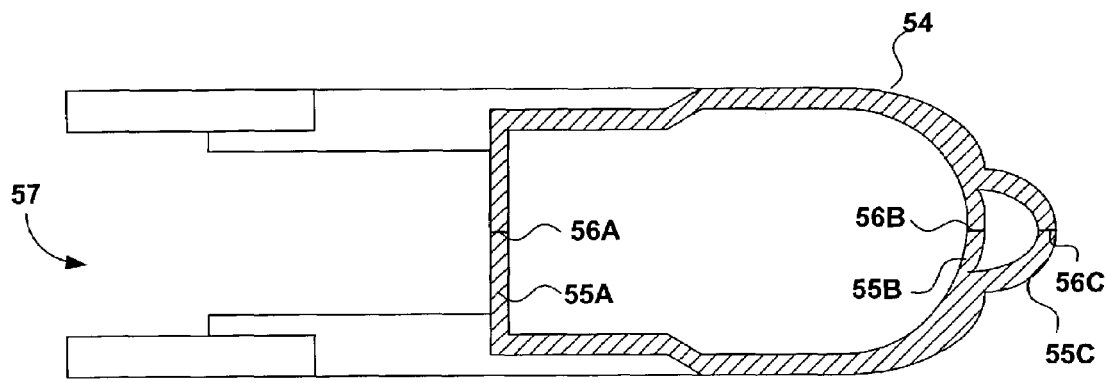

FIGS. 4 and 5 are enlarged cross-sectional views of distal ends (second ends) of exemplary outer lead bodies that may correspond to outer lead body 36 of FIG. 3. As shown in FIG. 4, outer lead body 48 is formed with a seal 44 on its distal tip. This seal 44 can be pierced by an inner lead upon insertion of the inner lead into conduit 47. Seal may be pre-slit with a resealable slit 45 to simplify piercing through seal 44. Seal 44 may define a spring force about slit 45 upon piercing slit 45 with an inner lead. Accordingly, seal 44 can help ensure that minimal fluid, tissue, proteins, and/or cells are able to enter conduit 47 upon insertion of outer lead body 48 into a patient and may define a good fluid-tight seal upon being pierced by an inner lead. Seal 44 may also be very useful in limiting or avoiding fibrous tissue growth between an inner lead and outer lead body 48.

Outer lead body 48 may also include a metal portion 49, such as a metal band, in proximity to the distal end in order to facilitate location in the human body via an electromagnetic radiation source. Other radio opaque material may also be used to realize portion 49, including for example, a metal powder molded with the plastic lead body 48. In any case, X-rays, radio waves, or other electromagnetic radiation may be used to pinpoint portion 49 within a patient, allowing a physician to implant outer lead body 48 in a desired location with great accuracy. By way of example, portion 49 may comprise a platinum material welded to a major portion 46 of outer lead body 48. Major portion 46 may have sufficient rigidity to ensure that it will not collapse under pressure of anchoring structure 19 (FIG. 1) or a medical suture used to anchor outer lead body 48 in a location within a patient. A relatively rigid layer of material (not shown) may be used to form part of major portion 46 to provide such strength, particularly in locations where a suture would likely be used. Major portion 46 may also include a coiled layer (not shown) to avoid collapse of major portion if major portion 46 it is bent during the implantation of outer lead body 48.

FIG. 5 illustrates an alterative configuration of outer lead body 58 formed with a redundant seal 54 on its distal tip. In particular, the redundant seal 54 defines a plurality of sealing structures 55A, 55B, 55C that can be pierced by an inner lead upon insertion of the inner lead into conduit 57. Such redundant sealing can further ensure that fluid does not enter conduit once sealing structures 55A–55C have been pierced by an inner lead. Each of the plurality of sealing structures 55A, 55B, 55C may be pre-slit with respective resealable slits 56A, 56B, 56C to simplify piercing through the respective seal.

Figure 6:
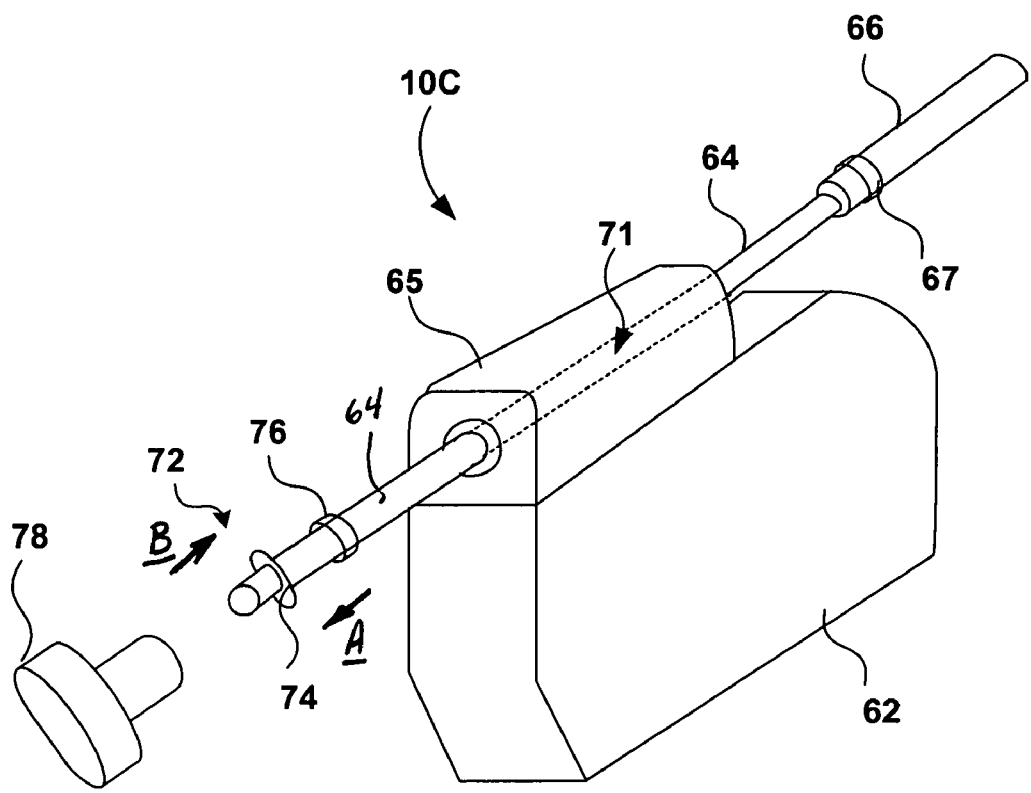
FIG. 6 is a perspective view of one embodiment of an IMD.

FIG. 6 is a perspective view of an IMD 10C. As shown in FIG. 6, IMD 100 comprises a housing 62 and an electrochemical lead assembly including an inner lead 64 and an outer lead body 66. As illustrated in FIG. 6, housing 62 includes a connector module 65 that facilitates electrical coupling of inner lead 64 to circuitry within housing 62. Outer lead body 66 is formed with a conduit that mates with inner lead 64. Accordingly, upon implantation of outer lead body 66, inner lead 64 can be removably inserted into the conduit of outer lead body 66. Thus, if inner lead 64 wears out, a new inner lead can be inserted in its place with a very non-invasive subcutaneous medical procedure that is less traumatic to a patient than conventional replacement procedures.

Outer lead body 66 includes a sealing structure 67 to facilitate a sealed engagement with connector module 65. FIG. 6 illustrates outer lead body pulled back from connector module so that sealing structure 67 may be seen. Connector module 65 includes a channel 71 through which inner lead 64 can be removed from IMD 10C, e.g., by pulling on the proximal end 72 of inner lead 64, per arrow A, to slide inner lead 64 from the conduit of outer lead body 66 and through channel 71. In other words, inner lead 64 may be removed from the conduit of outer lead body 66 through channel 71 of connector module 65. A new inner lead, also identified as item 64, can then be inserted, per arrow B, through channel 71 and into the conduit of outer lead body. In that case, outer lead body 66 may not need to be removed from connector module 65.

As further illustrated in FIG. 6, the proximal end of inner lead 64 may also be formed with a sealing ring 74 to seal against connector module 65. In addition, inner lead 64 may also include a mechanical stop 76 to ensure that proximal end of inner lead 64 cannot be inserted too far into connector module 65. An end cap 78 may be provided to cover the proximal end 72 of inner lead 64, e.g., by screwing onto connector module 65.

Figure 7:
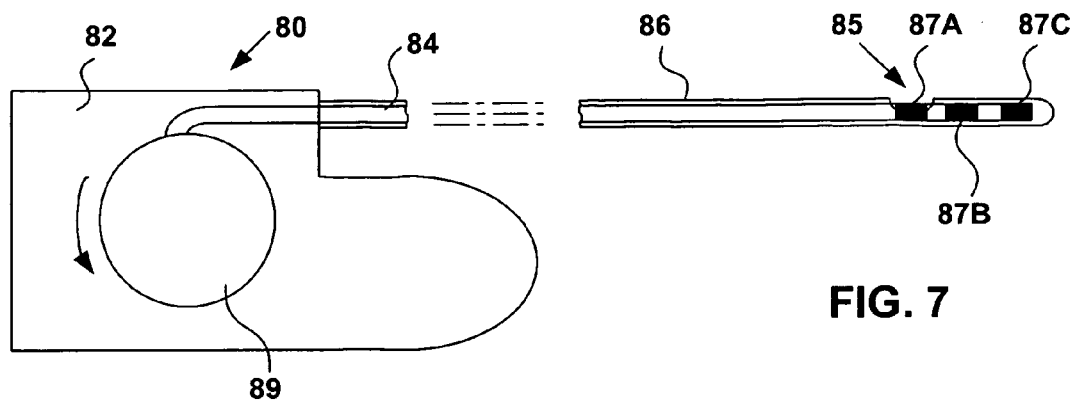
FIGS. 7–10 are cross-sectional side views of embodiments of IMDs.

FIG. 7 is a cross-sectional side view of another embodiment of an IMD 80. In the example of FIG. 7, IMD 80 comprises a housing 82 and a electrochemical lead assembly including an inner lead 84 and an outer lead body 86. Inner lead 84 defines a lead body that includes a plurality of electrochemical sensors 87A–87C formed along axial positions of the lead body in proximity to a distal end of inner lead. The proximal end of inner lead may include one or more electrical contacts (not shown).

For example, each of the electrochemical sensors 87A–87C may be electrically coupled to the electrical contact area on the proximal end. In some cases, the electrical contact may define a plurality of electrical contact areas formed at axial positions along the length of the lead body in proximity to the proximal end. Each of the electrochemical sensors 87A–87C is electrically coupled to a corresponding one or more of the plurality of electrical contact areas. Electrical components housed in housing 82 can be electrically coupled to electrochemical sensors 87A–87C so that sensed conditions can be stored or logged by the circuitry.

Outer lead body 86 may be formed with a window 85 in proximity to a distal end of outer lead body 86. Seals (not shown) may seal an exposed portion of inner lead 84 at window 85 from the conduit of outer lead body. In other words, seals may be provided in proximity to window 85 to seal an exposed sensor from the conduit and to seal non-exposed sensors from patient fluids and the like.

One of sensors 87 can be positioned relative to window 85 for sensing purposes. Moreover, IMD 80 may be caused to rotate reel 89 or a similar structure, to expose a new electrochemical sensor, e.g., sensor 87B to window 85 This rotation of reel 89 or a similar structure may be performed in response to a physician activated programming routine, mechanical screwing by the physician, or automatically activated rotation by IMD 80 upon determining that sensor 87A has worn out. If IMD 80 causes automated rotation of reel 89, IMD 80 may include a motor for performing such rotation. In any case, such repositioning of sensors 87 of inner lead 84 relative to window 85 of outer lead body 86 can provide sensor replacement with an atraumatic medical procedure, or possibly no medical procedure.

Figure 8:
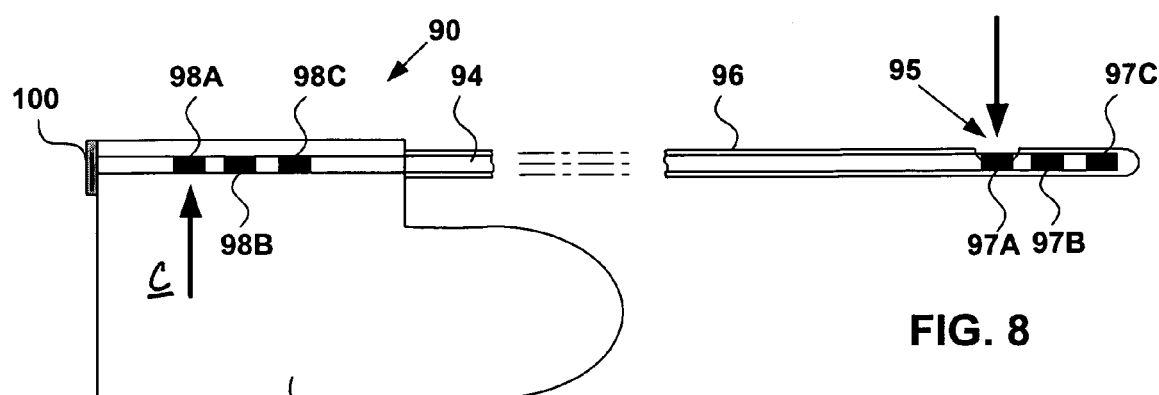
Figure 9:
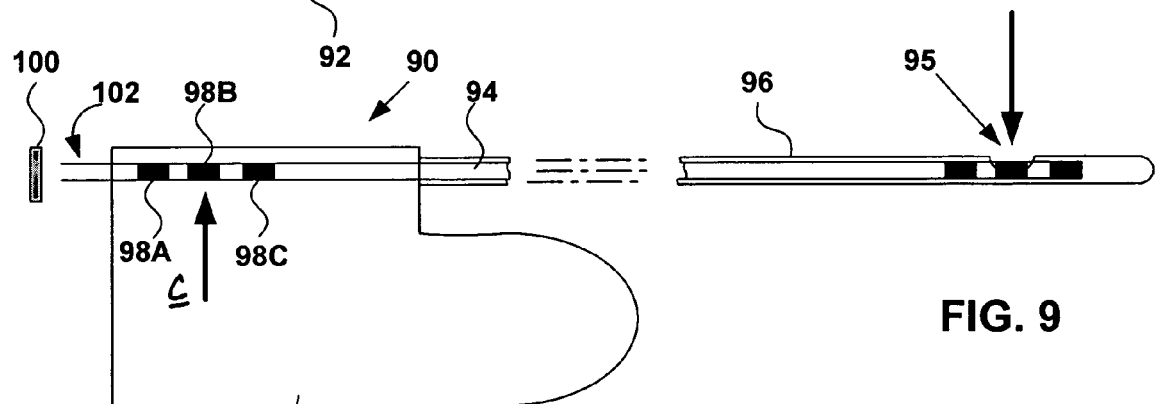
Figure 10:
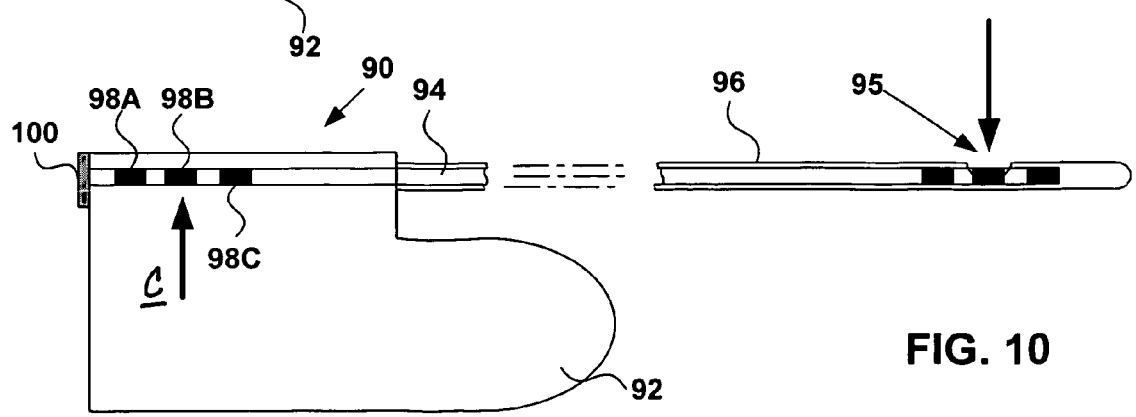

FIGS. 8–10 illustrate another configuration of IMD 90. As shown in FIGS. 8–10, IMD 90 comprises a housing 92 and a electrochemical lead assembly including an inner lead 94 and an outer lead body 96. Inner lead 94 defines a lead body that includes a plurality of electrochemical sensors 97A–97C formed along axial positions of the lead body in proximity to a distal end of inner lead 94. The proximal end of inner lead 94 may include one or more electrical contacts areas 98A–98C. For example, each of the electrochemical sensors 97A–97C may be electrically coupled to a corresponding one of the plurality of electrical contact areas 98A–98C. In any case, electrical components housed in housing 82 can be electrically coupled to electrochemical sensors 97A–97C so that sensed conditions can be stored or logged by the electrical components.

Outer lead body 96 may be formed with a window 95 in proximity to a distal end of outer lead body. One of sensors 97A can be positioned relative to window 95 for sensing purposes. When sensor 97A wears out, a relatively simple subcutaneous medical procedure may be performed in which a physician accesses housing 92, such as via a small incision into the patient. End cap 100 is removed as illustrated in FIG. 9, and inner lead 94 is repositioned by a physician relative to outer lead body 96. For example, inner lead 94 may be repositioned relative to outer lead body 96 to expose a new sensor 97B to window 95, and possibly to expose a new electrical contact area 98B to circuitry within housing 92. Contact area 98A may correspond to electrochemical sensor 97A, contact area 98B may correspond to electrochemical sensor 97B, and so forth. An electrical contact, shown as arrow C in FIGS. 8–10, within housing 92 may be positioned such that when a new sensor 97B is positioned relative to window 95, a corresponding electrical contact area 98B is positioned for electrical contact with circuitry in housing 92.

A portion 102 of inner lead 94 may be cut by the physician, and end cap 100 can be replaced as illustrated in FIG. 10. In this manner, a relatively simple electrochemical sensor replacement procedure can be used instead of more invasive conventional lead replacement procedures.

In still other embodiments, sensors may be positioned at a same axial location about the diameter of the inner lead. In that case, repositioning the inner lead with respect to the outer lead body may comprise rotating the inner lead relative to the outer lead body to expose a new sensor to a window of the outer lead body.

Figure 11:
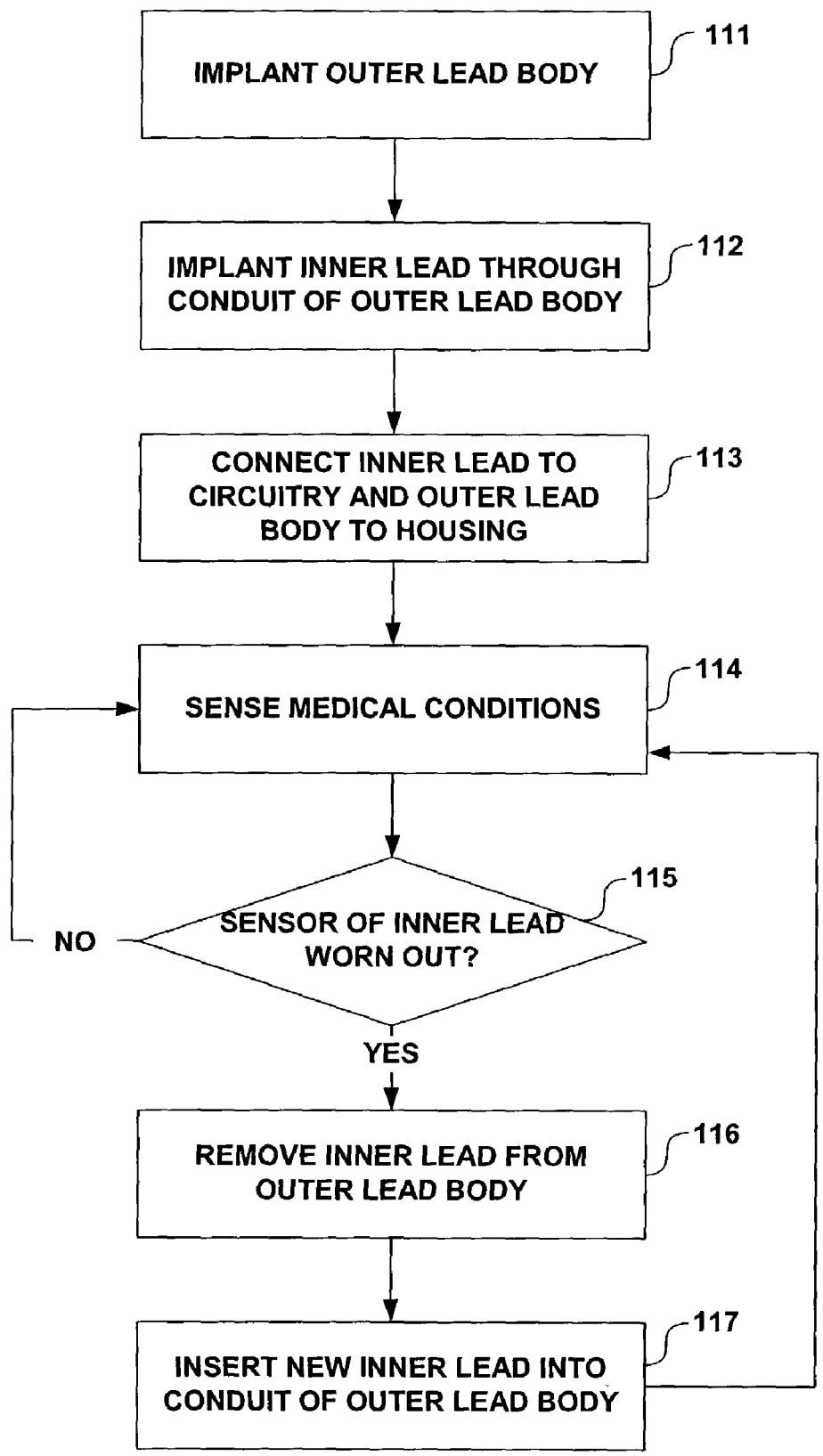
FIGS. 11 and 12 are flow diagrams illustrating sensor implantation and replacement techniques.
Figure 12:
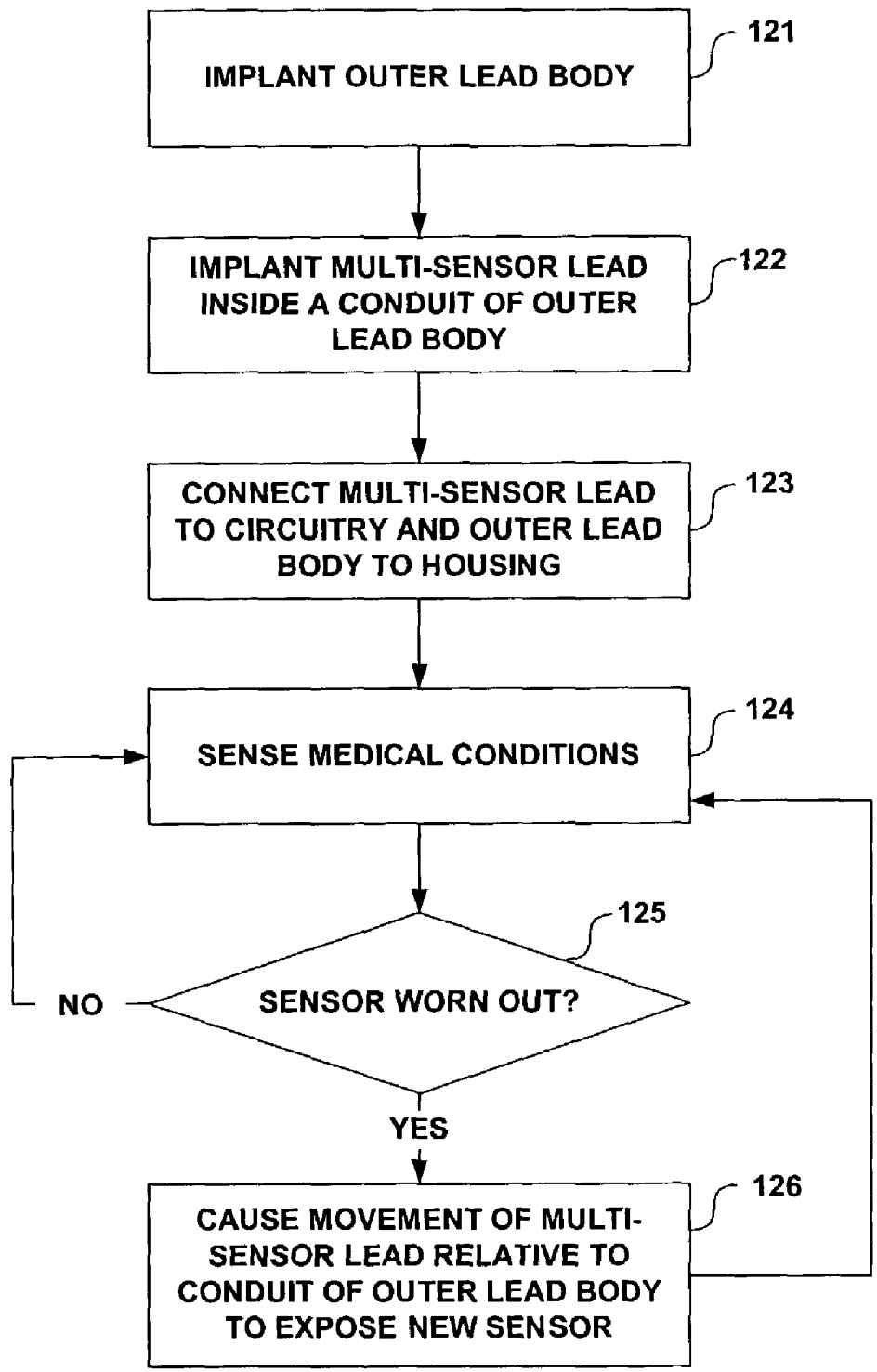

FIGS. 11 and 12 are flow diagrams illustrating sensor implantation and replacement techniques. FIG. 11 illustrates a sensor implantation and replacement technique in accordance with embodiments of the invention in which an IMD similar to those illustrated in FIG. 1, FIG. 2 or FIG. 6 is used. By way of example, IMD 10 of FIG. 1 will be used in describing FIG. 11. As illustrated in FIG. 11, a physician implants an outer lead body 16 in a substantially permanent location of the patient (111). In particular, the physician may insert outer lead body 16 through the superior vena cava and feed outer lead body 16 into a heart chamber. The outer lead body 16 may be secured to the patient by anchoring structure 19, e.g., to the connective tissues of the patient in proximity to the entry point of the superior vena cava. One or more sutures may also be used to secure outer lead body 16.

In order to position outer lead body in a proper location, the physician may use x-ray or radio wave techniques to locate a metal portion 49 (FIG. 4) of outer lead body 16. The physician then implants inner lead 18 through a conduit of outer lead body 16 (112). In particular, the physician can insert inner lead 18 through the conduit of outer lead body, eventually piercing a seal 44 or 54 (FIGS. 4 and 5) on the distal end of outer lead body 16. A lubricant may be added to inner lead 18 to improve the insertion through the conduit of outer lead body 16. Alternatively, the insertion of the inner lead into the outer lead body (112) may be performed prior to implantation of the outer lead body (111). In that case, both outer lead body and inner lead would be inserted into the patient at the same time. In any case, physician may use Fluorscopy to visualize a sensor location relative to a distal end of the outer lead body 18. Also, marks or radio opaque material on the inner lead may be used to help the physician location the correct implantation point.

Once both the inner lead 18 and outer lead body 16 have been successfully implanted, inner lead 18 and outer lead body 16 can be connected to a housing 12 of IMD 10 (113). The inner lead 18 may be electrically coupled to circuitry within housing 12, and outer lead body 18 may be coupled to housing 12. Outer lead body 18 may be formed with one or more structures on a proximal end to ensure a tight seal at housing 12, yet still allow for removal and reattachment of outer lead body 18 to housing 12 at a later time.

IMD 10 can then be used to sense medical conditions within the patient (114). Specifically, an electrochemical sensor, such as a glucose sensor, on a distal end of inner lead 18 may be used to sense conditions. Electrical signals may be affected by such chemical processes to identify such conditions. The sensed conditions may be stored by circuitry within housing 12, and possibly telemetrically transmitted to a programmer so that a physician can interpret the meaning of the sensed conditions and diagnose the patient accordingly.

Eventually, the electrochemical sensor of inner lead 16 may wear out (yes branch of 115). As mentioned, the relatively short useful life of electrochemical leads is a major concern. Once the electrochemical sensor of inner lead 16 has depleted or become overgrown with tissue, a relatively simple and non-invasive procedure may be performed to replace inner lead 16. Specifically, the physician can remove inner lead 16 from outer lead body 18 (116), and a new inner lead can be inserted in the conduit of outer lead body 18 (117). Again, the physician may use Fluorscopy to visualize a sensor location relative to a distal end of the outer lead body 18. Also marks or radio opaque markers on the new inner lead may be used to help the physician location the correct implantation point.

Such a removal and replacement procedure may be much less invasive than conventional electrochemical sensor lead replacement procedures. By leaving outer lead body 18 permanently implanted, new inner leads can be easily inserted. Only a relatively small incision may be required to access housing 12 so that, for example, inner lead 16 may be removed from conduit of outer lead body 18 through channel 71 and a new inner lead may be inserted through channel 71 and into conduit of outer lead body 18. Alternately, outer lead body 18 can be unattached, and inner lead 16 can be pulled from the conduit of outer lead body. If desired, anchoring structure 19 may be removed during the replacement procedure and then reattached following replacement of inner lead 16.

Also, during the replacement procedure it may be desirable to flush outer lead body 18, e.g. with a saline solution following removal of inner lead 16 and prior to insertion of a new inner lead. In addition, an anti-inflammatory agent, such as a steroid may be provided on the distal end of the new inner lead, e.g., to help limit or avoid fibrous tissue growth onto the new inner lead. An anti-biotic agent may also be used to flush the outer lead to help avoid patient infections.

FIG. 12 illustrates a sensor implantation and replacement technique in accordance with embodiments of the invention in which an IMD similar to those illustrated in FIG. 7–10. By way of example, IMD 80 of FIG. 7 will primarily be used in describing FIG. 12. As illustrated in FIG. 12, a physician implants an outer lead body 86 in a substantially permanent location of the patient (121). Like the procedure of FIG. 11, the physician may insert outer lead body 80 through the superior vena cava and feed outer lead body 16 into a heart chamber. The outer lead body 86 may be anchored by anchoring structure and one or more sutures may also be used. Outer lead body 86 may include a rigid layer in a section where a suture or anchoring structure can be applied to avoid collapse of outer lead body when a suture is applied.

In order to position outer lead body 86 in a proper location, the physician may use x-ray or radio wave techniques to locate a metal portion or other radio opaque material (similar to 49 of FIG. 4) of outer lead body 86. The physician then implants a multi-sensor inner lead 84 through a conduit of outer lead body 86 (122). Alternatively, the insertion of multi-sensor inner lead 84 into outer lead body 86 (122) may be performed prior to implantation of outer lead body 86 (121). The physician may use fluoroscopy to visualize a sensor location relative to a distal end of the outer lead body 86. Also, marks on multi-sensor inner lead 84 may be used to help the physician locate the correct implantation point. The proper implantation point may correspond to a location in which sensor 87A aligns with window 85.

Once both the multi-sensor inner lead 84 and outer lead body 85 have been successfully implanted, multi-sensor inner lead 84 can be connected to circuitry and outer lead body 86 can be connected to a housing 82 of IMD 80 (123). Outer lead body 86 may be formed with one or more structures on a proximal end to ensure a tight hermetic seal at housing 82.

IMD 10 can then be used to sense medical conditions within the patient (124). Specifically, a sensor 87A proximate to window 85, such as an electrochemical sensor may be used to sense conditions. The sensed conditions may be stored by circuitry within housing 82, and possibly telemetrically transmitted to a programmer so that a physician can interpret the meaning of the sensed conditions and diagnose the patient accordingly.

Eventually, sensor 87A may wear out (yes branch of 125). Once sensor 87A wears out, multi-sensor inner lead 86 can be moved relative to the conduit of outer lead body to expose a new sensor, e.g. sensor 87B, to window 85. For example, a proximal end of lead 86 may be coupled to a reel 89. Reel 89 may be caused to move, such as via programming signals sent from a physician, physical rotation by the physician, or possibly automatic movement caused by IMD 80 itself. In any case, rotation of reel 89 can cause a new electrochemical sensor, e.g. sensor 87B to be positioned relative to window. In this manner, sensor replacement can be greatly simplified.

Alternatively, rather that use a reel 89, a configuration of IMD 90 like that illustrated in FIGS. 8–10 may be used. In that case, a physician can remove end cap 100 and pull on inner lead 94 by a sufficient amount to move sensor 97B into alignment with window 95. The physician can then cut portion 102 and replace the end cap 100 as illustrated in FIG. 10.

A number of embodiments and features have been described. The techniques and structures may find useful application in any scenario where sensors on medical leads have a relatively shore life span and the patient condition requires long term monitoring beyond the useful life span of the sensor. Many details of the invention have been provided in the context of an electrochemical glucose sensor. However, the invention may find usefulness in a wide variety of sensor applications, particularly non-electrode sensing applications in which tissue overgrowth or depletion cause the useful life of the sensor to be limited. For example, the invention may be useful for electrochemical sensors, optical sensors, pressure sensors, blood borne biochemical or chemical sensors, lactate sensors used in the coronary sinus to detect ischemia, sensors for measuring CKMB, sensors for measuring Troponin I, T and C, sensors for measuring Myoglobin, sensors for measuring BNP (P-type natriuretic peptide), Micro Electro Mechanical Systems (MEMS) sensors or other types of medical sensors for which replacement during the life of the patient is anticipated. These and other embodiments are within the scope of the following claims.

What is claimed is:

1. A method comprising:
   coupling a first end of a sealing structure to a first lead;
   coupling a second end of the sealing structure to a connector module;
   removing the first lead including a first sensor from an implanted outer lead body through a channel in a connector module of an implantable medical device housing; and
   inserting a second lead including a second sensor into the implanted outer lead body.

* * * * *